United States Patent
Arnold et al.

(10) Patent No.: US 7,175,810 B2
(45) Date of Patent: *Feb. 13, 2007

(54) PROCESSING OF PARTICLES

(75) Inventors: Don W. Arnold, Livermore, CA (US); David J. Rakestraw, Livermore, CA (US); Phillip H. Paul, Livermore, CA (US); Patrick Pak-Ho Leung, Belmont, CA (US)

(73) Assignee: Eksigent Technologies, Dublin, CA (US)

( * ) Notice: Subject to any disclaimer, the term of this patent is extended or adjusted under 35 U.S.C. 154(b) by 23 days.

This patent is subject to a terminal disclaimer.

(21) Appl. No.: 10/849,715

(22) Filed: May 19, 2004

(65) Prior Publication Data

US 2004/0235181 A1  Nov. 25, 2004

Related U.S. Application Data

(63) Continuation-in-part of application No. 10/295,482, filed on Nov. 15, 2002.

(51) Int. Cl.
G01N 33/48 (2006.01)

(52) U.S. Cl. ............... 422/73; 422/68.1; 422/82.05; 436/63; 436/164; 436/165; 436/180

(58) Field of Classification Search ............ 436/63, 436/52, 53, 164, 165, 172; 422/68.1, 73, 422/81–82, 82.05, 82.08
See application file for complete search history.

(56) References Cited

U.S. PATENT DOCUMENTS

| 3,143,691 A | 8/1964 | Hurd | 317/231 |
|---|---|---|---|
| 3,427,978 A | 2/1969 | Hanneman et al. | 103/1 |
| 3,923,426 A | 12/1975 | Theeuwes | 417/48 |
| 6,086,243 A | 7/2000 | Paul et al. | 366/273 |
| 6,277,257 B1 | 8/2001 | Paul et al. | 204/450 |
| 6,406,848 B1 | 6/2002 | Bridgham et al. | 435/6 |
| 2003/0091475 A1 | 5/2003 | Yu et al. | 422/99 |
| 2004/0072278 A1* | 4/2004 | Chou et al. | 435/29 |

FOREIGN PATENT DOCUMENTS

| WO | WO 00/12123 | 3/2000 |
|---|---|---|
| WO | WO 01/38865 | 5/2001 |
| WO | WO 01/85341 | 11/2001 |
| WO | WO 03/085379 | 10/2003 |

OTHER PUBLICATIONS

Brenner, S. et al., *Nature Biotechnology* 18:630-634 (2000).
Sato, K. et al., *Anal. Chem.* 72:1144-1147 (2000).

* cited by examiner

*Primary Examiner*—Maureen M. Wallenhorst
(74) *Attorney, Agent, or Firm*—Anna Lynne Heinkel; T.H.P. Richardson; Sheldon & Mak (57) ABSTRACT

Particles dispersed in a liquid are assembled in a configuration in which all the particles lie in the same plane, and the assembled particles are processed while in that configuration. The assembled particles can for example be simultaneously exposed to electromagnetic radiation which elicits from the particles a response which provides information about the particles. The particles can for example be cells, cell fragments, or analyte-bearing beads of the type conventionally analyzed in a cytometer.

14 Claims, 10 Drawing Sheets

OFF-AXIS ILLUMINATION

FIG. 25

CONFOCAL ILLUMINATION

PROCESSING OF PARTICLES

CROSS REFERENCE TO RELATED APPLICATIONS

This application is a continuation-in-part of copending commonly assigned application Ser. No. 10/295,482, which was filed on Nov. 15, 2002, by Rakestraw, Arnold and Paul. This application also claims priority from International Patent Application Number PCT/US 03/36533, which was filed on Nov. 14, 2003, by Eksigent Technologies LLC and which claims priority from Ser. No. 10/295,482. The entire disclosure of each of those applications is incorporated herein by reference for all purposes.

BACKGROUND

The invention relates to the processing of particles, including but not limited to the examination of particles which are conventionally examined by cytometry.

Flow cytometry is widely used in life sciences research and clinical diagnostics for analyzing particles, including cells and beads having analytes attached thereto. A disadvantage of cytometry is that each particle must be examined individually. Other techniques for examining particles are disclosed in, for example, Nature Biotechnology (2000), 18, 630–634, Brenner, S. et al, and Anal. Chem. (2000), 72, 1144–1147, Kitamori, T. et al.

SUMMARY OF THE INVENTION

We have discovered, in accordance with the present invention, that particles dispersed in a liquid can be efficiently processed by assembling the particles in a configuration in which all the particles lie in the same plane, and processing the assembled particles while they are in that configuration. In a preferred embodiment of the invention, substantially all the particles are simultaneously exposed to electromagnetic radiation which elicits from the particles a response which provides information about the particles. In this preferred embodiment, the invention can be used to obtain analytical information about particles which is similar to the information provided by cytometry, but which can be obtained using apparatus which is simpler to make and use.

In a first preferred aspect, this invention provides a method of processing particles, the method comprising the steps of (A) placing a sample containing the particles dispersed in a liquid in a processing chamber containing a particle receptor;

(B) causing at least some of the particles in the placed sample to be received by the particle receptor so that the received particles are all in the same plane; and (C) processing at least some of the particles received by the particle receptor.

The method can include the step of (D) removing the particles from the processing chamber so that the processing chamber can be reused. Alternatively, the processing chamber containing the particles can be discarded after step (C), thus avoiding all danger of residual material interfering with reuse of the processing chamber. As discussed below, the particles in the sample may undergo physical and/or chemical change in step (C). The term "removing the particles" in step (D) is used to include removing the particles in the original or in a changed state.

In a second preferred aspect, this invention provides a novel processing chamber comprising (i) a sample inlet;

(ii) an elongate particle retention passage (EPRP) which is in fluid communication with the inlet and which has a first end and a second end; and (ii) between the first and second ends of the EPRP, an elongate particle receptor comprising an elongate barrier member which permits passage of liquid but not the passage of the particles to be processed, e.g. particles having a size greater than a selected size in the range of 0.1 to 50 micron, preferably a size greater than a selected size in the range of 1 to 20 micron.

In such a processing chamber, the particle-bearing liquid can be directed towards the barrier member, so that the particles are received by the particle receptor and the liquid passes beyond the barrier member, as in the method of the first aspect of the invention In a third preferred aspect, this invention provides apparatus for carrying out the method of the first aspect of the invention, the apparatus comprising a processing chamber according to the second aspect of the invention and means for processing particles received by the receptor, preferably a source of electromagnetic radiation which elicits from the particles a response which provides information about the particles. The term "apparatus" is used in a wide sense to include any system comprising a plurality of cooperating parts.

BRIEF DESCRIPTION OF THE DRAWINGS

The invention is illustrated in the accompanying drawings, which, with the exception of FIGS. 26–27, are diagrammatic and not to scale, and in which.

DETAILED DESCRIPTION OF THE INVENTION

In the Summary of the Invention above, in the Detailed Description of the Invention and the claims below, and in the accompanying drawings, reference is made to particular features of the invention, including for example components, ingredients, devices, apparatus, systems, steps and embodiments. It is to be understood that the disclosure of the invention in this specification includes all possible combinations of such particular features. For example, where a particular feature is disclosed in the context of a particular aspect or embodiment of the invention, or a particular Figure, or a particular claim, that feature can also be used, to the extent possible, in combination with and/or in the context of, other particular aspects and embodiments of the invention, and in the invention generally. The invention claimed herein includes the use of features which are not specifically described herein, but which provide functions which are the same as, equivalent to or similar to, features specifically described herein.

The term "comprises", and grammatical equivalents thereof, are used herein to mean that other components, ingredients, steps etc. are optionally present in addition to the component(s), ingredient(s), step(s) specifically listed after the term "comprises". For example, a system "comprising" (or "which comprises") components A, B and C can contain only components A, B and C, or can contain not only components A, B and C, but also one or more other components. Where reference is made herein to a method comprising two or more defined steps, then, unless the context requires otherwise, the defined steps can be carried out in any order or simultaneously, and the method can include one or more other steps which are carried out before any of the defined steps, between two of the defined steps, or after all the defined steps. The term "at least" followed by a number is used herein to denote the start of a range beginning with that number (which may be a range having an upper limit or no upper limit, depending on the variable being defined). For example "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)", this means a range whose lower limit is the first number and whose upper limit is the second number. The numbers given herein should be construed with the latitude appropriate to their context and expression. The terms "plural" and "plurality" are used herein to mean two or more. The term "elongate" is used herein to refer to an article or passageway having one dimension (its length) which is substantially greater than, preferably at least 4 times, e.g. at least 6 times, each of its other dimensions. The abbreviation "EPRP" is used herein to refer to an elongate particle retention passage.

Where reference is made herein to "a", "an", "one" or "the" feature, it is to be understood that, unless the context requires otherwise, there can be a single such feature or more than one such feature. For example, when reference is made herein to a feature selected from a list of features, it is to be understood that, unless the context requires otherwise, the feature can be a single one of the listed features or two or more of the listed features.

When reference is made herein to a first feature and/or a second feature, it is to be understood that, unless the context requires otherwise, such terminology is used for convenience in identifying such features, and means that either or both features can be present, and that when both features are present, they can be the same or different.

Where reference is made herein to two or more components (or parts or portions etc.), it is to be understood that the components can be, unless the context requires otherwise, separate from each other or integral parts of a single structure or a single component acting as the two or more specified components.

Particles

A wide variety of particles can be used in the present invention, and they can be dispersed in any suitable liquid. Typically, but not necessarily, the particles are from about 0.1 to about 50, for example from about 1 to about 20, micron in diameter. The particles are usually, but need not be, of substantially the same size. The sample can contain for example from about 5 to about 25,000 particles per microliter. Thus, depending on the size of the sample, the number of particles in the sample can for example be up to 5000, for example 50 to 5000, e.g. 100 to 1000.

The particles can for example be particles of the kind used in cytometry. Such particles include naturally occurring materials, e.g. cells and cell fragments, and particles which contain one or more sites which have interacted with one or more analytes. The particles may also contain one or more characteristic features which, when the particle is examined under appropriate conditions, identify the particle as belonging to a particular class. Such characteristic features include, for example, the presence of known amounts of one or more dyes which will fluoresce in a characteristic waveband when illuminated by a suitable laser. Other characteristic features include size, shape, reflectivity, density, radioactivity, color, electrical charge, magnetic properties, the presence of optodes, and the presence of fluophores which cease to fluoresce under the examination conditions. Analytes which can be examined in this way include electrolytes, metabolite molecules, enzymes, antibodies, antigens, and polynucleotide fragments.

For disclosure of particles used in cytometry and their examination, reference may be made for example to U.S. Pat. Nos. 4,499,052, 4,665,020, 5,736,330, 5,747,349, 5,981,180, 6,057,107, 6,139,800, 6,165,790 and 6,271,042, European Patent No. 126,450 and UK Patent No. 1,561,042.

Preparation, Pretreatment, and Dilution or Concentration of Samples

The sample can be prepared from the sample source in any way. For example, a multi-port rotor valve can be connected to the sample source, a pump, a sample loop, a waste reservoir, and a delivery conduit. In a first position of the valve, particle-containing liquid is pumped from the sample source into the sample loop (the amount of liquid preferably being greater than that required to fill the sample loop, in order to ensure that the loop is completely filled); the excess liquid flows to the waste reservoir. In a second position of the valve, the sample is pumped down the delivery conduit towards the processing chamber.

In some cases, it may be desirable to wash and/or to modify the particles in the sample before the sample is delivered to the processing chamber. In such cases, the sample can for example be passed into a pretreatment chamber through which liquid can pass, but which retains the particles, e.g. an elongate pretreatment chamber which includes a barrier member of the kind used in the processing chamber. The particles can be exposed to a single liquid or sequentially to two or more liquids. The liquid(s) can merely wash the particles to remove unwanted components of the original sample, for example excess components of an assay mixture, and/or can produce some desired change, e.g. a chemical reaction, in the particles, in which case the wash fluid flows across the particles for the length of time necessary to complete the reaction. A single reaction or a series of reactions can be carried out. The progress of the reaction(s) can in some cases be monitored by observing signals from the particles (for example if appropriate fluors are added as part of the reaction sequence). The treated particles can be removed from the pretreatment chamber by a reverse flow of a suitable liquid.

In some cases, it may be desirable to increase or decrease the concentration of particles in the sample before the sample is delivered to the processing chamber. In such cases, the sample can be delivered to a dilution chamber in which additional liquid is added to it. If the particles have been washed or otherwise pretreated, they can be flushed out of the pretreatment chamber into a dilution chamber having a volume corresponding to the desired concentration.

For example, if the EPRP contains 100 to 500 particle parking sites and has a volume between 4 and 20 nL, a preferred sample contains about 25,000 particles per microliter. To obtain such a concentration from an original sample containing about 300 particles in a volume of 25 microliters, the particles in the original sample are separated, e.g. by causing the liquid in the original sample to pass over a weir which retains the particles, and are then flushed into a dilution chamber having a suitable volume (e.g. with a volume in the tens of nL range, depending upon the design of the EPRP).

Processing Chambers

The invention can make use of any processing chamber containing a particle receptor such that at least some, preferably substantially all, of the particles received by the particle receptor are in the same plane. However, the invention will chiefly be described by reference to processing chambers according to the second aspect of the invention, i.e. processing chambers comprising
 (i) a sample inlet,
 (II) an elongate particle retention passage (EPRP), and
 (iii) between the ends of the EPRP, an elongate particle receptor including an elongate barrier member which permits passage of the liquid but not the particles.

Elongate Particle Retention Passages (EPRP's)

Figure 15:
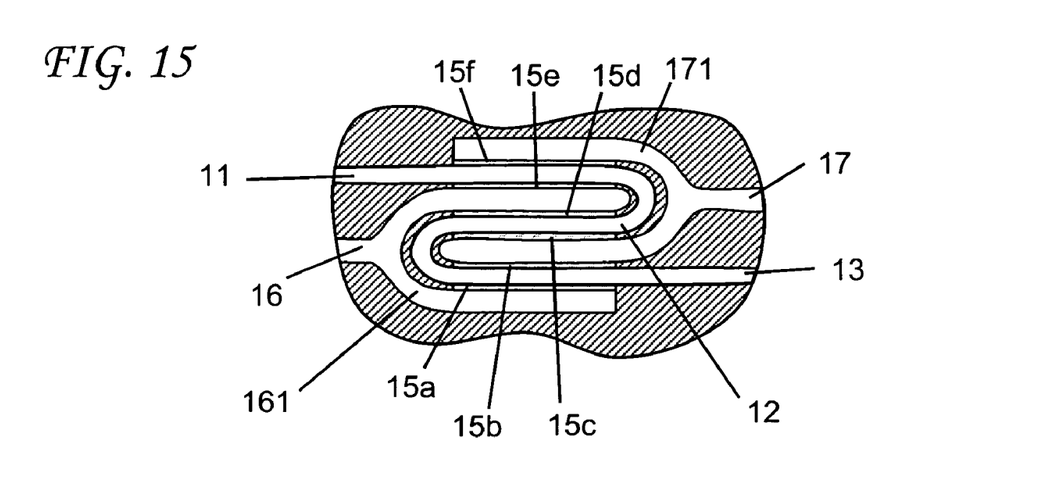
FIG. 15 is a cross-section of a serpentine processing chamber.

The EPRP can be straight; or can include straight and curved portions, thus forming for example a serpentine shape as shown for example in FIG. 15; or can be continuously curved. The cross-section of the EPRP, which is preferably constant, can be of any shape, e.g. part-round or rectangular (including square). The passage may have, for example, transverse dimensions in the range of about 10 to about 100 micron, e.g. a width of about 40 to about 100 micron and a depth of 10 to 50 micron, such that the particle-bearing liquid can freely flow therethrough, while minimizing the volume of the sample. Preferably each of the transverse dimensions of the EPRP is at least about 2.5 times, particularly at least about 4 times, the particle size.

The EPRP can be in any orientation relative to the horizontal, since gravitational forces play little or no part in the operation of processing chamber. However, for the purposes of defining the EPRP, it can conveniently be regarded as comprising an elongate base, an elongate top, and two opposed elongate walls at least one of which comprises an elongate particle receptor including the elongate barrier member. The base and/or top can merge into one or both of the walls, so that there is no line of demarcation between them.

The base and/or top and/or one or both of walls of the EPRP can be shaped so that particles are guided towards the desired configuration. For example, the wall can have a concave arcuate cross-section ending at or near the top of the barrier member and/or the top can include an elongate retention member which is adjacent to and at an angle, e.g. substantially at a right angle, to the face of the barrier member, so as to form an elongate corner which helps to retain the particles in the desired configuration.

When each wall comprises a particle receptor, this makes it possible to reverse the direction in which particle-bearing liquid flows (either during the examination of a single sample, or for the examination of different samples) or because one of the particle receptors has become unusable, for example because it has become contaminated. The use of two opposed particle receptors is also useful when an electrical or magnetic field causes different particles in the sample to move in opposite directions. In other embodiments, the other elongate wall is for example solid or apertured, preferably so that the particles cannot pass through it.

Figure 14:
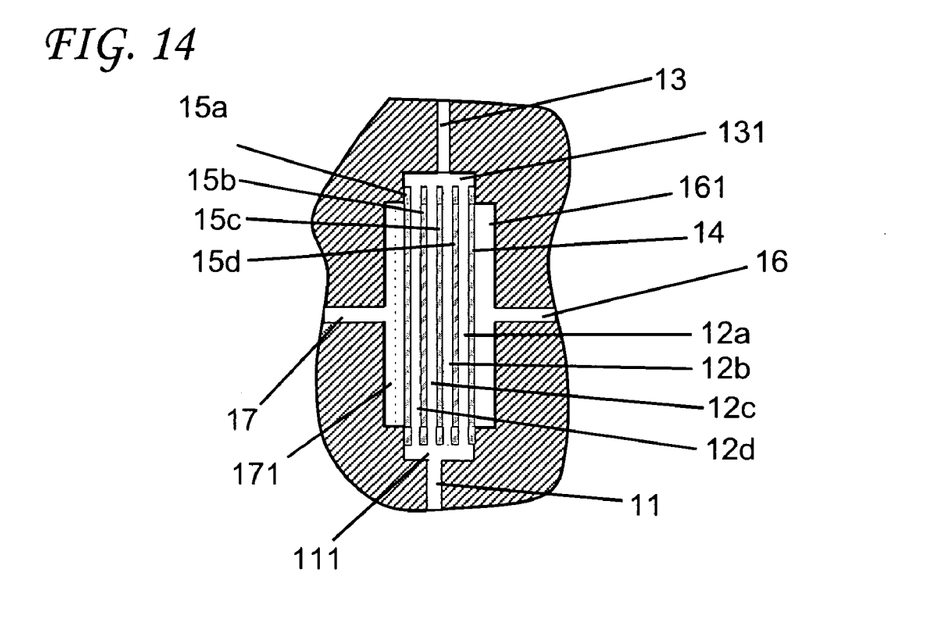
FIG. 14 is a cross-section of a processing chamber comprising four EPRP's.

The processing chamber can comprise a single EPRP or a plurality of EPRP's which lie in the same plane and which are preferably parallel to each other. When the processing chamber comprises a plurality of EPRP's, adjacent EPRP's can share an elongate wall which provides an elongate particle receptor to one or both of the EPRP's. An example of such a processing chamber is shown in FIG. 14. When the processing chamber comprises a plurality of EPRP's, all of them can be in liquid communication with a single inlet, or there can be a plurality of different inlets, each communicating with one or more of the EPRP's.

Auxiliary Chambers

The processing chamber can include at least one elongate auxiliary chamber which runs alongside the EPRP and (i) receives liquid which has passed over or through the barrier member or (ii) serves as a reservoir for liquid to be delivered into the EPRP. If there are plural parallel EPRP's sharing adjacent elongate walls, the auxiliary chambers run alongside the outermost EPRP's. The auxiliary chambers improve the uniformity of the processing along the length of the EPRP's.

Barrier Members

In preferred embodiments of the invention, the barrier member is a weir, the clearance gap above the weir being less than the size of particles which are to be retained. The particles, when directed against the weir, are received in a line at the top of the weir. In other embodiments, for example, the barrier member has a plurality of conduits which traverse the barrier member and provide the only way in which liquid can pass through the barrier member, the size of the conduits being such that the particles to be retained cannot pass through them. For example, 2×2 micron square conduits will prevent the passage of any particle larger than 2 micron in diameter. The conduits are preferably placed in a line at the top of the barrier member, so that the particles are received in a line at the top of the conduit-containing barrier member.

Pockets for Receiving Particles

The barrier member and/or the retention member can optionally be shaped to assist in the location of individual particles in the desired configuration, for example can comprise a plurality of pockets, each of the pockets being capable of receiving one, but only one, of the particles. Such pockets can be placed on, or be an integral part of, the barrier member and/or the retention member. They are preferably placed and shaped so that they do not otherwise impede particle flow during step (A) and during any step which is carried out to remove the particles from the processing chamber. The pockets can be spaced at intervals which assist in interrogation of particles located therein. The pockets may be at least 5%, preferably at least 10%, larger than the maximum dimension of the particles in the sample, but less than twice the smallest dimension of the particles, to prevent two particles from being received by the same pocket. Generally, the pockets have a maximum depth of about 2 to about 20 micron and a width of about 3 to about 15 micron. The number of pockets may be for example from about 100 to about 1500. The number of pockets may be for example from 1.5 times to 3 times the number of particles reaching the barrier member.

Manufacture of Processing Chambers

The processing chamber can conveniently be made by sealing together a bottom member and a top member. Before being sealed together, the members are shaped in any convenient way (e.g. by machining, including laser machining, water jet machining or bead jet abrasive machining; injection molding; embossing; or wet or dry chemical etching), to provide the inlet, EPRP and elongate particle receptor, and any other desired components. The processing chamber can be made of any convenient material, remembering, however, that when the processing of the particles involves exposing the particles to electromagnetic radiation, and/or results in a signal in the form of electromagnetic radiation, the relevant parts of the processing chamber must be sufficiently transparent to that radiation, e.g. will transmit at least 40%, preferably at least 60%, of that radiation.

In some embodiments, the top and bottom member of the processing chamber, although sealed together, are separable. A single bottom member can then be used with a selected one of a number of different top members, or vice versa. In this way, if only one of the top and bottom members includes pockets for locating particles, it can be replaced by a different member having differently-sized pockets, when there is a change in the size of particles to be processed. In addition, if either member becomes contaminated or damaged, it can be replaced.

Inlets and Outlets in the Processing Chambers

In some embodiments, the processing chamber has a sample inlet at one end and a sample outlet at the other end. In other embodiments, the sample inlet is also used as an outlet for the particles after they have been processed. The processing chamber can also contain other ports, for example for entry and exit of positioning fluid.

Causing Particles to be Received by Receptors

In some embodiments, a positioning liquid is used to direct the particles towards the receptors. In these embodiments, the processing chamber preferably includes an inlet and an outlet for the positioning liquid, the inlet and outlet being placed so that positioning liquid passing between them flows in a direction generally transverse to, preferably substantially at right angles to, the axis of the EPRP, thus directing the particles towards the particle receptor. The inlet and outlet for the positioning liquid are preferably separated from the adjacent side wall by auxiliary chambers (as described above) which act as flow diffusers, and help the positioning liquid to act uniformly over the length of the EPRP. The volume of positioning liquid used for this purpose can be more than, equal to, or less than, the volume of the sample. The positioning liquid can be one whose only function is to direct the particles towards the receptors, or it can be one which in addition produces some desired change in the particles or the liquid in the sample. It should not of course damage (i.e. cause some unwanted change in) the sample. For example, for most biological samples, appropriate saline conditions should be maintained. After the particles have been processed, the flow direction of the positioning liquid can be reversed to assist in the removal of the particles from the EPRP.

As an alternative to, or in addition to, the use of a positioning liquid, the flow of the liquid sample itself into and through the EPRP can be used to direct the particles into the particle receptors. This can be done for example by appropriate arrangement of the EPRP or EPRP's relative to the direction of flow of the sample from the inlet to an outlet of the processing chamber and/or by appropriately controlled pumping of the liquids within the processing chamber.

In one embodiment in which the flow of the liquid sample itself is used to direct the particles towards the particle receptor, the processing chamber comprises an inlet and an outlet, the inlet being connected to an entry conduit having a plurality of parallel coplanar EPRP's connected thereto. Each of the EPRP's (i) has a cross-section throughout its length such that one or more particles can enter and pass longitudinally down the EPRP, and (ii) has its axis at an angle to the axis of the entry conduit, so that particles can move from the conduit into the EPRP; the angle can vary widely, e.g. from 30 to 150°, but angles of 30 to 60°, e.g. 45°, are often convenient, so that particles follow an obtuse-angled path as they pass from the entry conduit into the EPRP Each of the transverse dimensions of the EPRP's (in this and also in other embodiments) is preferably at least about 2.5 times, e.g. at least about 4 times, the particle size. Liquid entering each of the EPRP's passes over the barrier member into an auxiliary chamber, and all the auxiliary chambers are connected to an exit conduit connected to the outlet. The outlet is optionally connected to a pump which helps to maintain a desired rate of flow and helps to draw particles into the EPRP's. There can be two or more coplanar sets of parallel, coplanar EPRP's. For example, that can be two sets in which the EPRP's are mirror images of each other and which share an exit conduit which runs between them. If each of the auxiliary chambers is substantially identical to, but a mirror image of, its associated EPRP, then the system can be operated with flow in the opposite direction, the exit conduit becoming the entry conduit, the entry conduit becoming the exit conduit, the auxiliary chambers becoming the EPRP's, and the EPRP's becoming the auxiliary chambers. Such an arrangement is shown in FIGS. 17–20.

In another embodiment, the processing chamber is connected to a plurality of pumps, each which can exert positive and/or negative pressure on liquids in the processing chamber so as to urge particles towards or away from the particle receptor. Preferably the processing chamber is connected to (1) a delivery pump which provides primary control of the rate at which the sample is delivered to the inlet of the processing chamber, and (2) first and second positioning pumps which provides primary control over the rate and direction at which positioning fluid flows across the EPRP.

The delivery pump can also provide primary control over the rate at which the particles are removed after they have been processed. Preferably, the processing chamber is also connected to an extraction pump which provides primary control over the rate at which liquid is removed from the EPRP. The term "primary control" is used above because the way in which the other pumps operated can also influence the various rates and directions of liquid flow.

The different pumps can be controlled by electropneumatic actuators to provide a desired sequence of liquid flows within the processing chamber. With a correct configuration, sample can be fed and then positioned at the same time to the analysis chamber. For example, when loading a sample into the EPRP, there should be a positive pressure drop down the sample inlet line and a negative pressure drop (i.e. suction) down the outlet line. Particles in the sample can then be pushed towards the particle receptors. During this process, the sample outlet line can be pressurized to reduce or prevent liquid from leaving the EPRP. The selection of suitable pressure settings at different lines can assist in the removal of contaminants from the EPRP while minimizing the loss of sample particulates. We have found that it is useful, in particular in reducing contamination of the EPRP, to remove a minor proportion of the liquid sample from the EPRP during at least part of one or more of steps (A)–(C). The rate of removal can for example be 0.05 to 0.2 times the rate at which the sample is supplied during step (A).

In suitable pressure-controlled configurations, multiple electro pneumatic actuators can be used to provide pressure heads over a wide operating pressure range (typically 0–100 psi.), making it possible to use high flow rates for processing large volume of sample and/or cleaning. For example, the pressure can be set at 0 to 60 psi at different lines to get a pressure drop up to 60 psi for sample loading, and up to 100 psi at inlet and positioning outlet lines to provide maximum flush for releasing a sample. A relatively large amount (e.g. 10 to 20 µL.) of sample fluid can be processed in a short period of time (e.g. less than 1 minute). The sample-loading and sample-releasing processes can be repeated in a cyclic manner to process small portions in multiple cycles. Alternatively, all the particles can be captured in one sample-loading process. In the one-time capture mode, processing is simple and only a single detection step is needed after the sample-loading step is stopped. However, long sample loading times tend to capture small substance in the sample which sticks to the particles and particle receptors, and which can make it difficult to remove the particles in the releasing step. In the cyclic loading mode, less small sticky substance is captured, and the particles are relatively easy to remove. Multiple detection steps are needed for multiple cycles of loading, and the control of the cycle steps can be complicated if there is significant transient delay in the fluidic system.

In some embodiments, the particles have electrical properties such that an electrical or magnetic field can alternatively or additionally be used to direct the particles towards the receptors. The particles may have different electrical properties and, therefore, respond differently to the electrical or magnetic field, e.g. move in opposite directions.

Techniques for Processing Received Particles

Particles received by the particle receptors can be processed by any appropriate technique. In one embodiment, a multiplicity, preferably substantially all, of the received particles are interrogated simultaneously to provide information about the particles. Such interrogation often includes exposing the particles to electromagnetic radiation, e.g. from a laser, which interacts with the particles to produce a signal, for example a light signal resulting from one or more fluorescent dyes attached to, or infused into, the particles. Alternatively or additionally, the interrogation can be based on the size, shape, morphology, or reflectivity of the particles. It is also possible to apply a voltage to the particles on the receptors, and thus to generate an electrochemical signal or an electrochemically generated optical signal (through chemiluminescence). The signal is generally observed by a detector, but in some cases can be visually observed. The techniques used in cytometry can be used for this purpose. However, in cytometry each particle must be examined separately, whereas in the present invention any number (and preferably all) of the received particles can be examined simultaneously. This makes it possible to use a diffuse source of electromagnetic radiation, e.g. from a laser which is not focused as in cytometry or from an LED. The examination can be carried out very rapidly, e.g. in a few seconds or less, and the resulting signal can be analyzed while one sample is removed from, and a new sample placed into, the processing chamber.

Preferably the cross-sectional area illuminated by the electromagnetic radiation matches the cross-sectional area of the received particles. Because substantially all the particles lie in the same plane, detectors which collect 2D images can be used to monitor how the particles respond to processing. A plurality of lasers or other light sources can be used in parallel. Detectors which can be used include CCD cameras, CID cameras, diode arrays, and photographic film.

Figure 26:
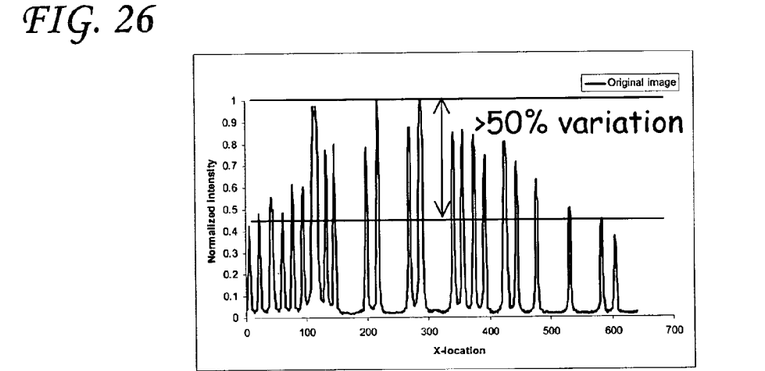
FIGS. 26 and 27 show the signals provided by particles when the signal depends upon the intensity of the illumination when no correction has been made for the intensity profile of the light source (FIG. 26) and when such correction has been made (FIG. 27)
Figure 27:
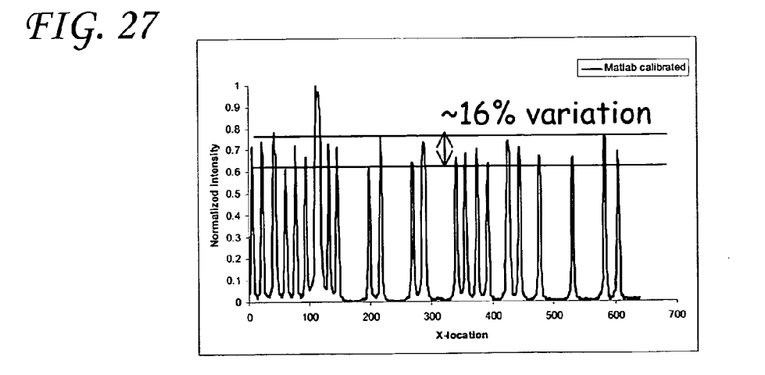

When the processing of the particles involves measuring the intensity of a signal generated by the particles, it is desirable to take steps which will at least partially correct for the intensity profile of the radiation source. This can be done, for example, in a separate normalization procedure in which (a) the light source to be used (or already used) to interrogate the particles illuminates an area which is similar to, preferably somewhat larger than, e.g. 25% larger than, the area containing the received particles, and which is composed of uniformly fluorescent material, e.g. a liquid or gel, and (b) the resulting signal is observed by the detection system to be used (or already used) when the particles are interrogated. The fluorescent area can for example be provided by a separate chamber which is physically attached to the processing chamber, or by a chamber which is used during the processing of particles, e.g. a dilution chamber, which is, however, disconnected and filled with the fluorescent material in order to carry out the normalization procedure. The results of this normalization procedure are used to normalize the signals obtained from the received particles of the sample. FIGS. 26 and 27 illustrate the improvement that can be obtained in this way.

Figure 21:
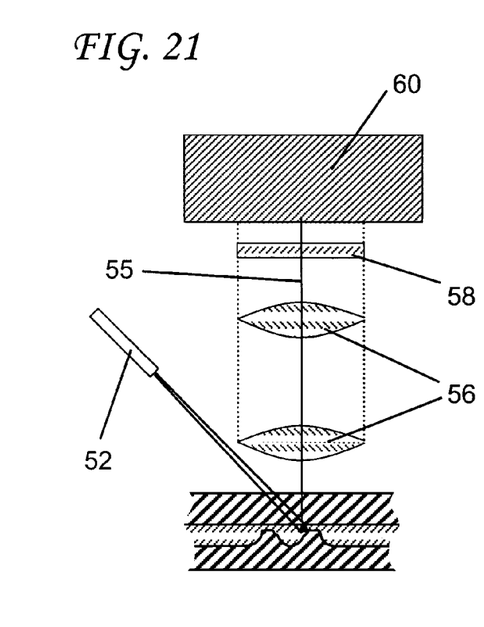
FIGS. 21–23 show the processing of retained particles in a processing chamber as shown in FIGS. 6–7 in order to identify the particles.
Figure 22:
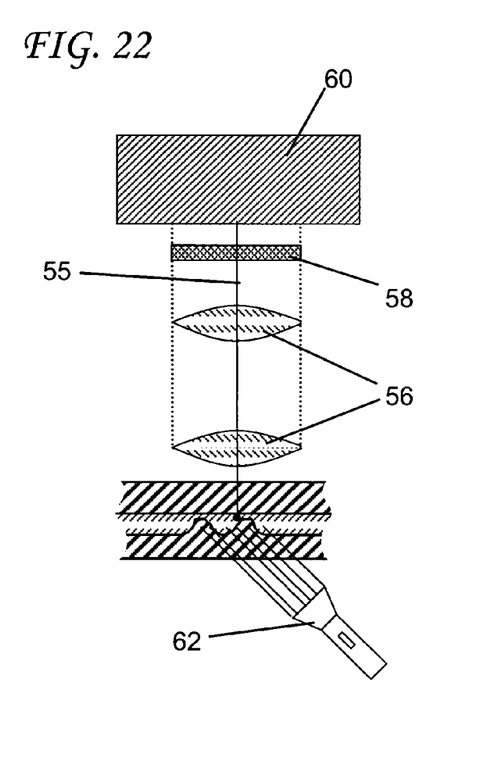

In some types of examination, fluorescence from the particles is observed along an axis which is different from the axis of the illumination, as shown for example in FIGS. 21 and 22. Such examination is referred to herein as off-axis examination. In other types of examination, the axes of observation and illumination are the same, as shown for example in FIG. 23. Such examination is referred to herein as confocal examination.

Figure 24:
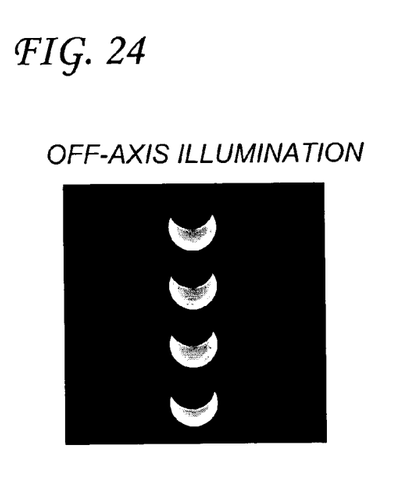
FIGS. 24 and 25 represent particles processed using different types of illumination.
Figure 25:
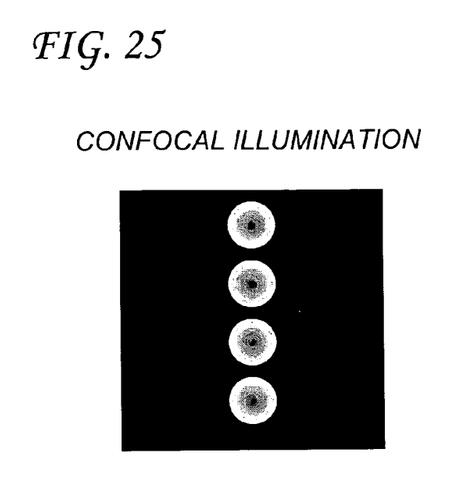

Off-axis examination results in an image which suffers from shadowing of one side of the particle. Confocal examination, on the other hand, provides a shadowless image. The different images are illustrated in FIGS. 24 and 25 These facts make it possible to use confocal examination to distinguish between (a) a particle whose response to the radiation is substantially uniform throughout the particle (e.g. a dye-infused particle), and which therefore produces an image whose intensity has a Gaussian profile brightest at the center, and (b) a particle whose response to radiation is only at the surface of the particle (e.g. a hybridized particle), and which therefore produces an image which is brighter at the periphery than at the center. This makes it possible to use a particle which is infused with an encoding dye and which, if it has reacted with an analyte, has been hybridized with a signal dye, the encoding and signal dyes responding differently to the radiation, e.g. producing different fluorescent signals when exposed to a laser. Such particles can be examined through a first filter to identify the encoding dye and then through a second filter to identify the concentration of the signal dye.

It is also possible for the received particles to be processed so that part or all of the particles (e.g. analyte fragments forming part of the particles) undergoes physical and/or chemical change, for example as a result of a single change, or a plurality of sequential changes, in the liquid which contacts the particles. When such processing results in a change in response of the particles to interrogation, it is possible to carry out kinetic measurements by monitoring the signal from the particles as a function of time. Thus, it is possible to use the method of the invention for chemical synthesis, using the particles as a solid phase support for the synthesis. The positioning fluid can be changed sequentially to effect desired chemical and/or physical changes to all or part of the received particles. The sequential changes in the positioning fluid are preferably effected in successive processing chambers, but can be effected in the same processing chamber. For example, a serial four-chamber system can sequentially introduce guanine, cytosine, thymine and adenosine for oligonucleotide synthesis.

It is also possible for the processing chamber to be used for sample preparation, re-concentration, extraction and clean up. Discrimination for low-concentrations of target analytes and high background analyte concentrations can be achieved by passing a sample over capture particles positioned in the processing chamber.

Pumps

Pumps are generally used to deliver and remove the liquid samples and, if positioning liquids are used, to control the flow of the positioning liquids. Preferably the pumps are pneumatic or electroosmotic (also known as electrokinetic) pumps. Such pumps can be precisely controlled and can accurately introduce very small quantities of liquid, e.g. about 100 picoliters to about 100 nanoliters of liquid per cycle. One or more of the pumps can act directly on the sample or positioning liquid. Alternatively or additionally, one or more of the pumps can comprise a flexible membrane (also known as a diaphragm) which is moved by working fluid and which is in contact with the sample or positioning liquid. This makes it possible to use a pump having a working fluid which would not be satisfactory to use as a positioning fluid or a pump which would not be satisfactory for the sample or positioning fluid. It also permits orthogonal control of the flow in the EPRP without cross-talk between the pumps. Suitable electroosmotic pumps are described for example in U.S. Pat. Nos. 6,277,257, 6,013,164 and 3,923,426, and copending, commonly assigned U.S. patent applications Ser. No. 10/273,723, filed Oct. 18, 2002 and Ser. No. 10/322,083, filed Dec. 17, 2002 and International Application No. PCT/US 03/32895, filed Oct. 17, 2003 , the entire disclosures of which are incorporated herein by reference. Any other suitable pump can be used, for example a syringe-type, piezo-actuated diaphragm, microbubble, pneumatic, or peristaltic pump. The pumps are preferably resistant to flow when they are in the off state, to prevent liquid leakage from the system.

Methods

The method of the first aspect of the invention involves steps (A)–(C) and optionally step (D). When step (D) is performed, the sequence of steps (A)–(D) is often repeated a number of times, using one or more fresh samples of the same composition, or one or more samples of one or more different compositions. It is also possible to carry out one or more or steps in addition to steps (A)–(C) and optionally step (D). For example, after the processing step (C) is complete, the direction of flow of the positioning fluid can be reversed before or during step (D) to assist in the removal of the particles from the receptors. A computer-controlled controller can be used to ensure that the various steps are carried out at defined time intervals.

Processing Chambers connected in Parallel and/or in Series

A plurality of processing chambers can be arranged in parallel and/or in series, preferably in a way such that several, and preferably all, of the particles received in a plurality, and preferably all, of the different processing chambers lie in the same plane and can, therefore, be examined simultaneously or can be examined sequentially in substantially the same way. Processing chambers connected in series are connected to a single inlet, so that they receive substantially identical samples; when a positioning liquid is used, it can be supplied from the same source but separately to each processing chamber through a manifold (as shown for example in FIGS. 13 and 14), or can be supplied to run sequentially through two or more processing chambers. When the processing chambers are connected in parallel, they can be connected to the same source of samples or to different sources of samples.

The number and size of the processing chambers, and the EPRP's which they contain, the size of the particles, and size of the pockets (if any) can for example be such that the number of retained particles in the same plane is for example 200 to 600 or higher, e.g. up to 2000 or even more.

Optionally, each processing chamber has its own valved sample inlet and outlet. Suitable microvalves are for example piezo-actuated diaphragm valves and the valves described in U.S. Pat. No. 6,019,882, U.S. Patent Publication No. 2002/0194909, and in copending commonly assigned U.S. patent application Ser. No. 10/666,466, filed Sep. 16, 2003 by Rehm et al, the entire disclosures of which are incorporated herein by reference. The processing chambers can be arranged in serpentine form, so that a plurality of rows of particles (which can be parallel to each other) can be processed simultaneously or sequentially in substantially the same way.

Connections

The connections between different parts of the systems and apparatus of the invention are preferably made using the techniques disclosed in the copending commonly assigned Provisional Application entitled Microfluidic Connector which was filed on Apr. 2, 2004, by Arnold et al, the entire disclosure of which is incorporated herein by reference.

Drawings

The invention is illustrated in the accompanying drawings, in which the same or similar components are denoted by the same reference numerals.

Figure 1:
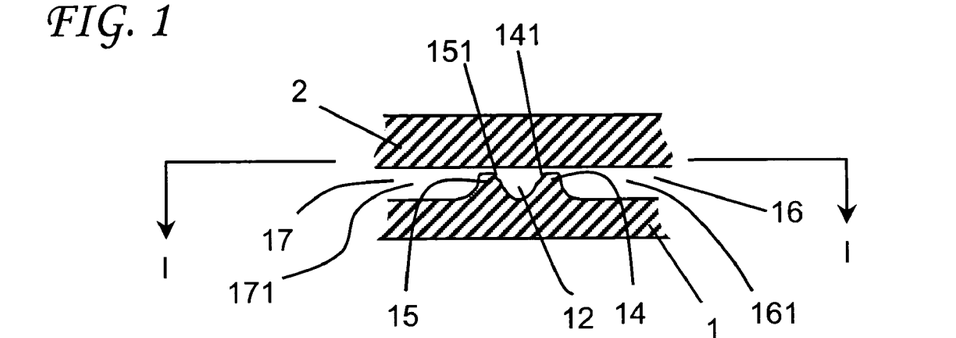
FIG. 1 is a cross-section of a processing chamber of the invention.
Figure 2:
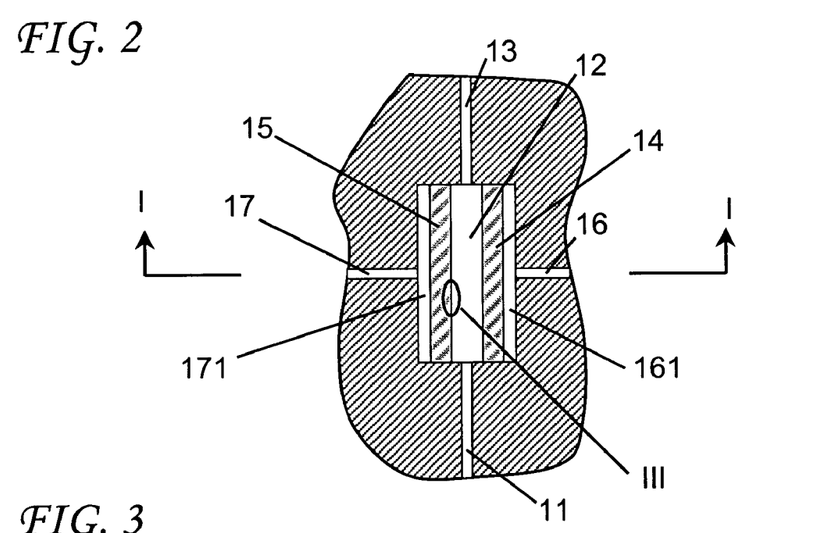
FIG. 2 is a cross-section on line I—I of FIG. 1.
Figure 3:
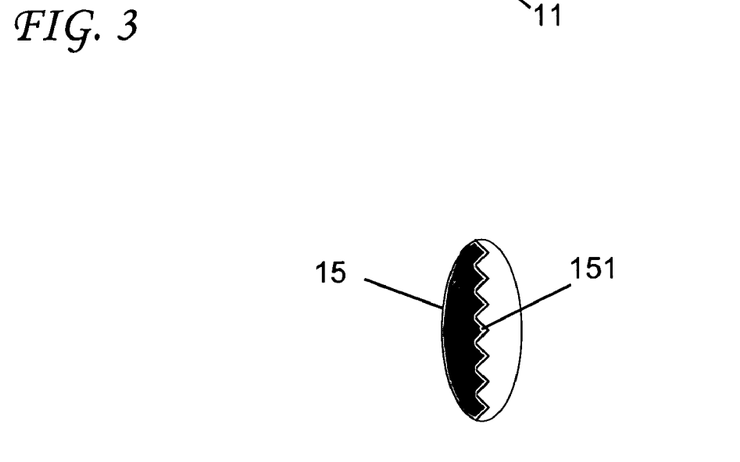
FIG. 3 is an enlarged cross-section of part of FIG. 2, FIGS. 4–5, 6–7, 8–9 and 10–11 are cross-sections showing successive stages in the operation of a processing chamber similar to that shown in FIGS. 1–3, FIGS. 12 and 13 are cross-sections showing a processing chamber similar to that shown in FIGS. 1–3.

FIG. 1 is a cross-section of a processing chamber of the invention. FIG. 2 is a cross-section on line I—I of FIG. 1. FIG. 3 is an enlarged cross-section of part of FIG. 2. As shown in FIGS. 1–3, the processing chamber comprises a bottom member 1 and a top member 2 sealed thereto. The bottom member comprises an EPRP 12 having a sample inlet 11 one end and a sample outlet 13 at the other end. The sidewalls 14 and 15 of the EPRP 12 are barrier members in the form of weirs having pockets 141 and 151 formed therein. The gaps between the tops of the weirs and the base of the top member 2 are such that liquid can pass through the gaps but the particles cannot. Positioning fluid inlet 16 communicates with auxiliary diffuser chamber 161 adjacent to the weir 14. Positioning fluid outlet 17 communicates with auxiliary diffuser chamber 171 adjacent to the weir 15.

Figure 4:
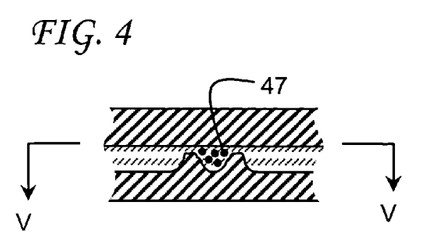
Figure 5:
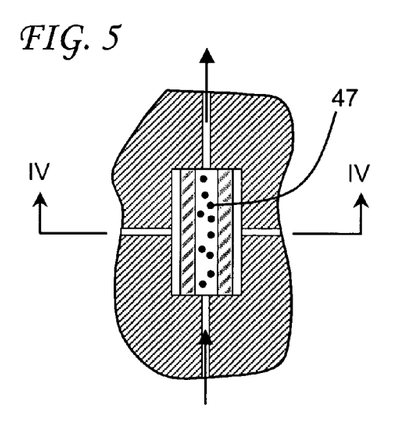
Figure 6:
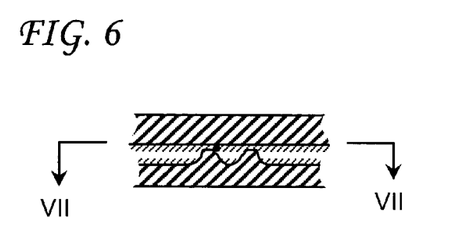
Figure 7:
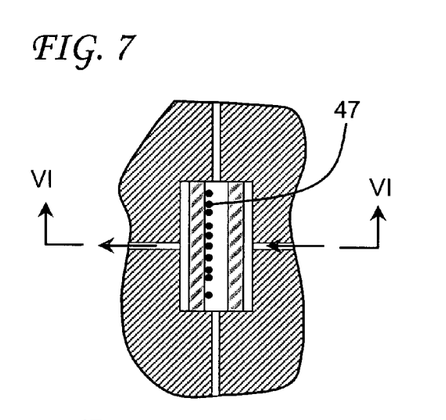
Figure 8:
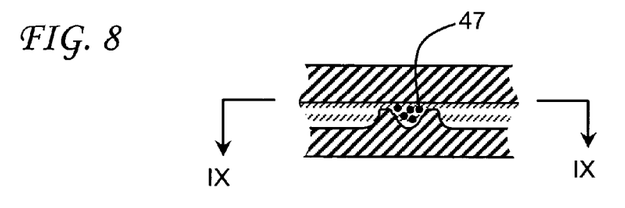
Figure 9:
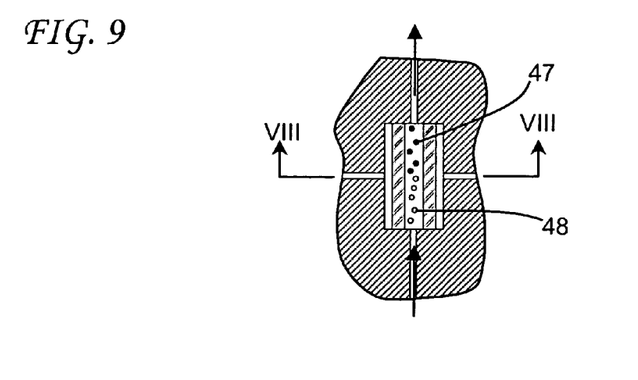

FIGS. 4–5, 6–7, and 8–9 are cross-sections showing successive stages in the operation of a processing chamber as shown in FIGS. 1–3, except that the particle receptors are only on the weir 15. In FIGS. 4–5, a sample bearing particles 47 has been introduced into the central passage. In FIGS. 6–7, introduction of the sample has ceased, and transverse flow of the positioning liquid has caused the particles to be received by the particle receptors. In FIGS. 8–9, after the particles have been processed, flow of the positioning liquid has ceased, and a fresh sample bearing articles 48 is being introduced through the sample inlet.

Figure 10:
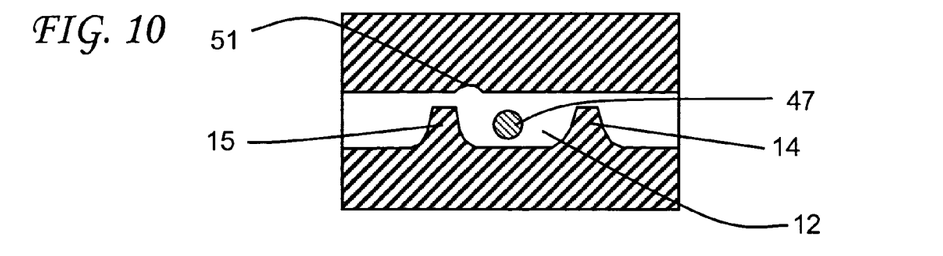
Figure 11:
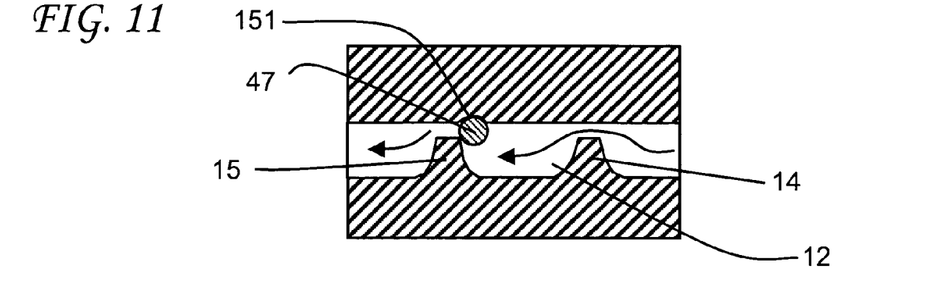

FIGS. 10 and 11 are partial cross-sections of a processing chamber in which here are pockets 151 in the top member 2 adjacent the weir 15.

Figure 12:
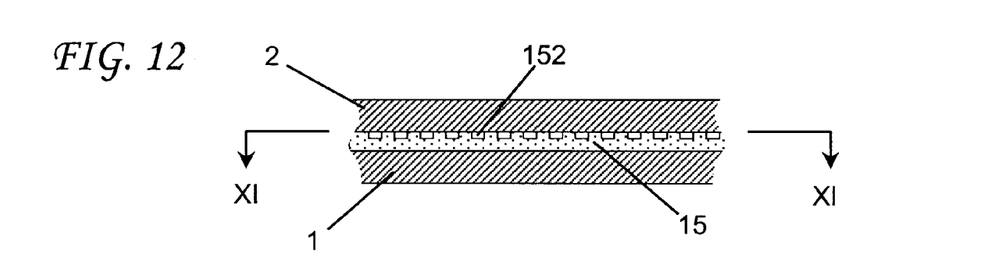
Figure 13:
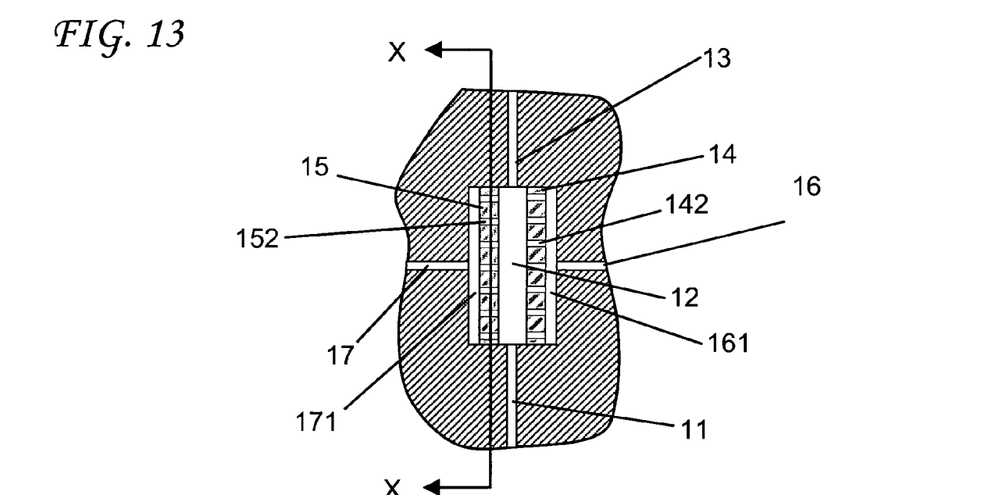

FIGS. 12 and 13 are cross-sections showing a processing chamber as shown in FIGS. 1–3, except that the barrier members 14 and 15 are in the form of apertured walls which contact the top member 2 and have channels 142 and 152 running through their top surface.

FIG. 14 is a cross-section of a processing chamber comprising four EPRPs 12a, 12b, 12c and 12d defined by parallel weirs 14, 15a, 15b, 15c and 15d. Mounted on the weirs 15a, 15b, 15c and 15d and/or in the top member adjacent to the weirs (but not shown in FIG. 12) are particle receptors like those shown in FIGS. 1–3 and 10–11. The sample to be processed is introduced through sample inlet 11 to manifold 111 and into the EPRP's, optionally via valves not shown in FIG. 12. Positioning fluid is introduced through inlet 16 into auxiliary diffuser chamber 161, and then passes sequentially through the elongate passages, the auxiliary diffuser chamber 171 and the outlet 17.

FIG. 15 is a cross-section of an EPRP having a serpentine shape. The sample is introduced into the EPRP through sample inlet 11 and leaves through sample outlet 13. Positioning fluid is introduced through inlet 16, passes through auxiliary diffuser chamber 161, over weirs 15a, 15d and 15e into EPRP 12, through EPRP 12, over weirs 15b, 15c and 15f into auxiliary diffuser chamber 171 and leaves through outlet 17.

Figure 16:
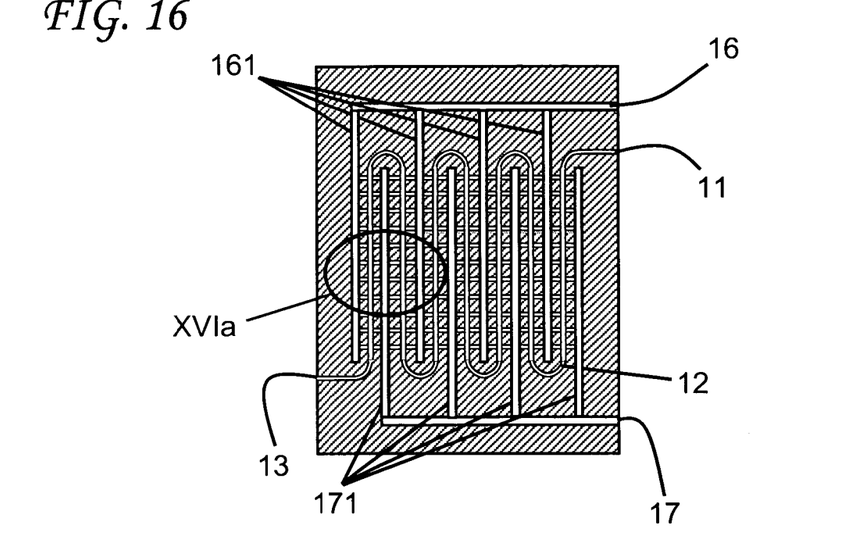
FIGS. 16 and 16A illustrate a system comprising a plurality of processing chambers.
Figure 16A:
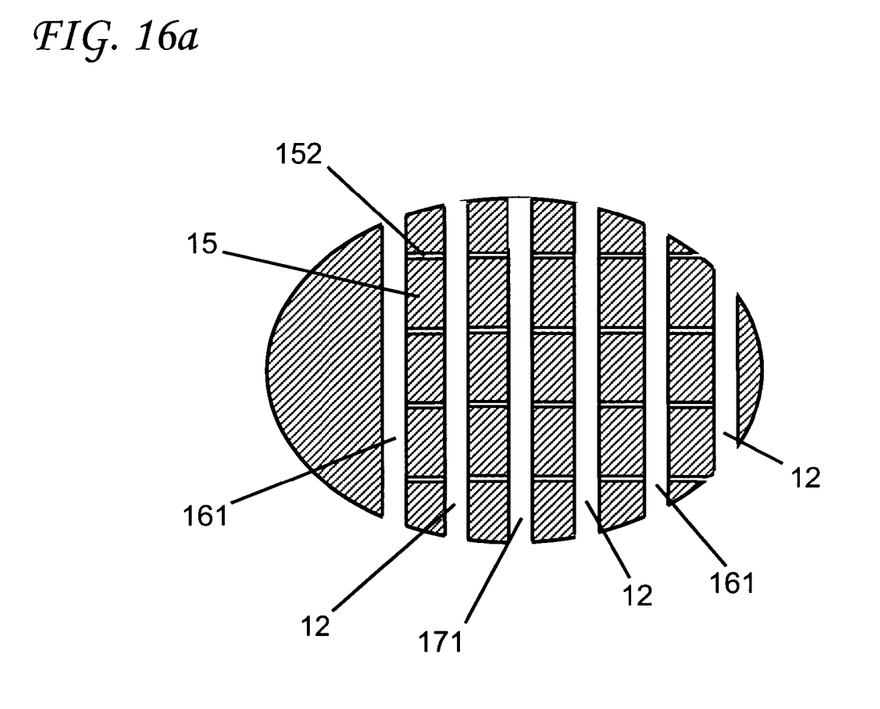
Figure 17:
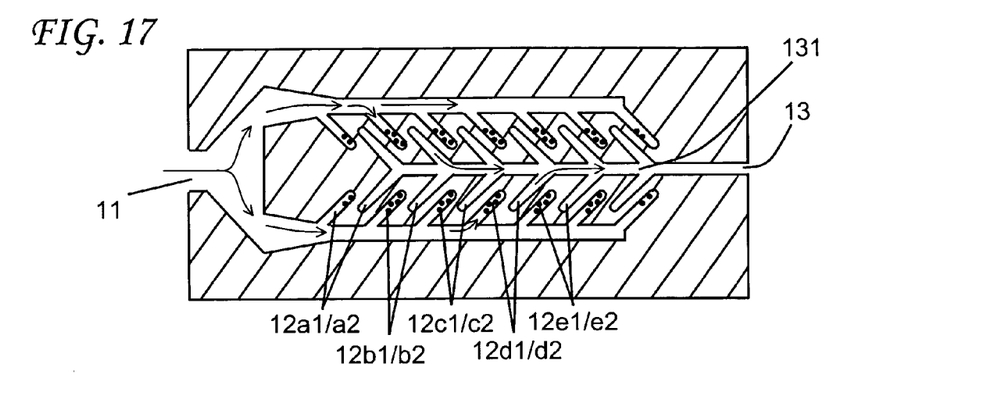
FIG. 17–20 are cross-sections through a processing chamber in which the flow of the liquid sample positions the particles.
Figure 18:
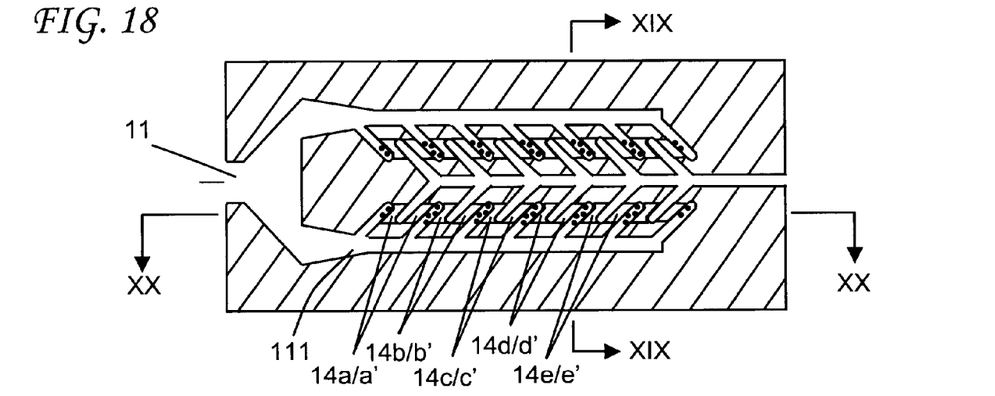
Figure 19:
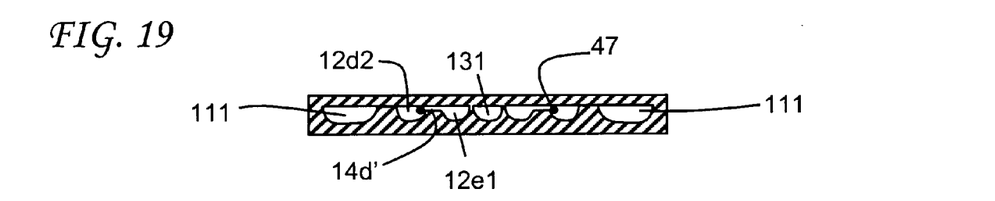
Figure 20:
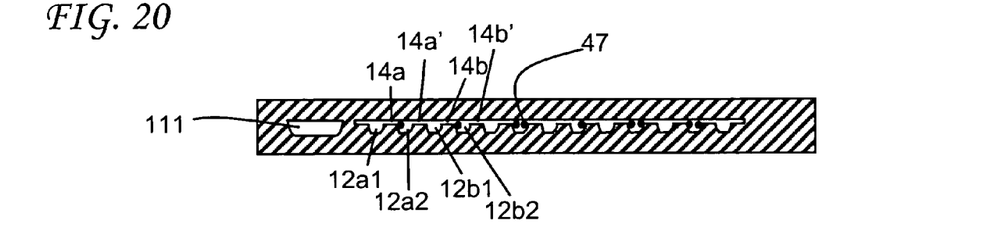

FIG. 16 is similar to FIG. 15, but has a much larger number of turns, so that a larger number of particles can be processed per cycle. The sample enters through inlet 11 and leaves through outlet 12. The positioning liquid enters through inlet 16 and leaves through outlet 17. FIG. 16A is an enlarged view of part of FIG. 16.

FIG. 17–20 show processing chamber in which the flow of the liquid sample positions the particles. EPRP's 12a1/a2,12b1/b2 . . . are arranged in pairs with parallel weirs 14a, 14b . . . between them. There are also parallel weirs 14a/a', 14b/b' . . . between the EPRP's 12a2 and 12b1, 12b2 and 12c1 . . . The first EPRP in each pair is connected at an angle to manifold 111 connected to inlet 11 for the particle-bearing sample. The second EPRP in each pair is connected at an angle to exit conduit 131, which is connected to outlet 13 for particle-free liquid which passes over the weirs into the second EPRP, which functions as an auxiliary chamber. The particles enter and travel down the EPRP's 12a1, 12b1 . . . and are retained on the weirs. After the received particles have been processed, they can be removed by reversing the liquid flow. The reverse liquid flow can be provided by a second particle-bearing sample, so that the second EPRP's retain the second particles, and the first EPRP functions as an auxiliary chamber FIG. 21 shows the processing of retained particles in a processing chamber as shown in FIGS. 6–7 in order to identify the particles. A laser 52 directs diffuse beam 54 having a selected wavelength through the top member 2 onto the retained particles. Light 55 is reflected or emitted from the particles, and after passing through appropriate optics 56 and filters 58 is detected and analyzed by detector 60.

FIG. 22 is similar to FIG. 21, except that a different diffuse light source such as an LED is used to interrogate the particles, and is directed through the bottom of the processing chamber.

Figure 23:
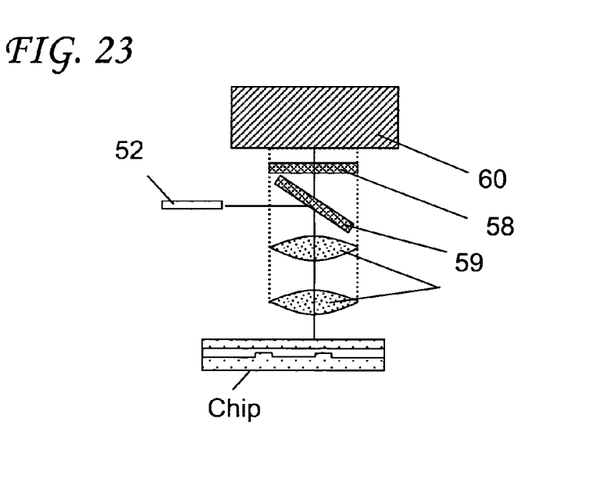

FIG. 23 shows confocal examination of particles retained in an EPRP. A laser 52 directs a diffuse beam having a selected wavelength at a dichroic reflector 59 and onto the particles via optics 56. Light emitted by the particles (at a different, typically longer, wavelength) is collected and analyzed by detector 60.

FIGS. 24 and 25 show typical results from the off-axis illumination (FIG. 24) and confocal illumination (FIG. 25) of particles retained by an EPRP.

FIG. 26 shows a typical result, when the signal from a particle depends upon the intensity of the incident light, for the intensity of the signal from a dye-infused particle when there has been no flat-field correction of the signal. FIG. 27 shows the same data when flat-field correction has been carried out.

Figure 28:
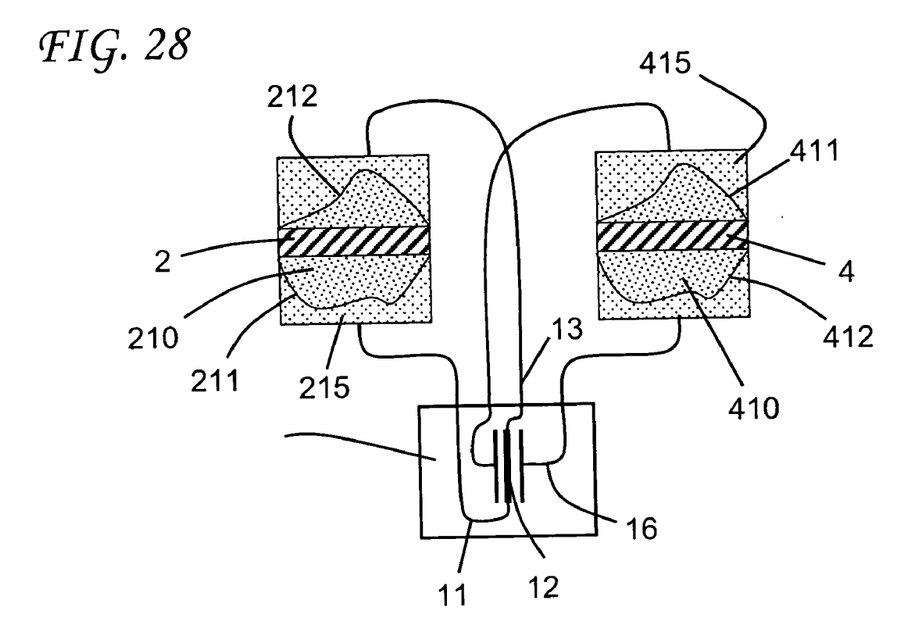
FIGS. 28 and 29 show pumping systems for delivering samples and positioning fluids to a processing chamber of the invention.

FIG. 28 shows the use of diaphragm-containing pumps to control the delivery and removal of samples and positioning fluids to a processing chamber. Sample pump 2 includes pump fluid 210 confined by diaphragms 211 and 212, movement of which pumps particle-bearing liquid 215 through a processing chamber containing EPRP 12. Sample pump 4 includes pump fluid 412 confined by diaphragms 411 and 412, movement of which pumps positioning fluid 415 through the processing chamber.

Figure 29:
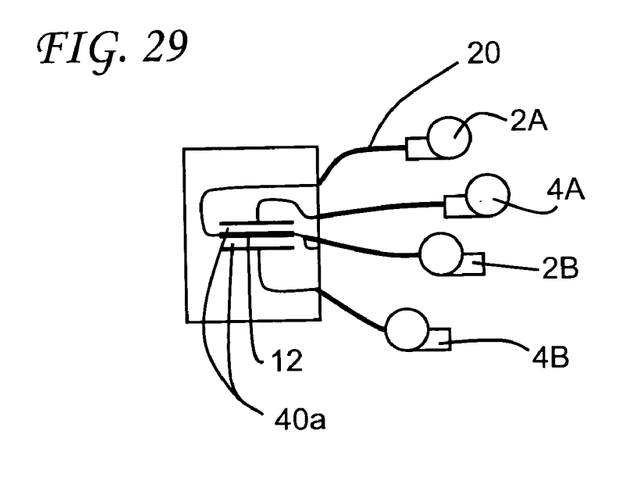

FIG. 29 shows the use of pumps 2A and 2B to control delivery and removal of the sample to an EPRP 12 and the use of pumps 4A and 4B to control delivery and removal of positioning liquid to the EPRP. The pumps can be under electropneumatic control, so that different pressures can be applied to different inlets and outlets simultaneously, according to a program which produces desired flow rates in different parts of the system at different times.

Figure 30:
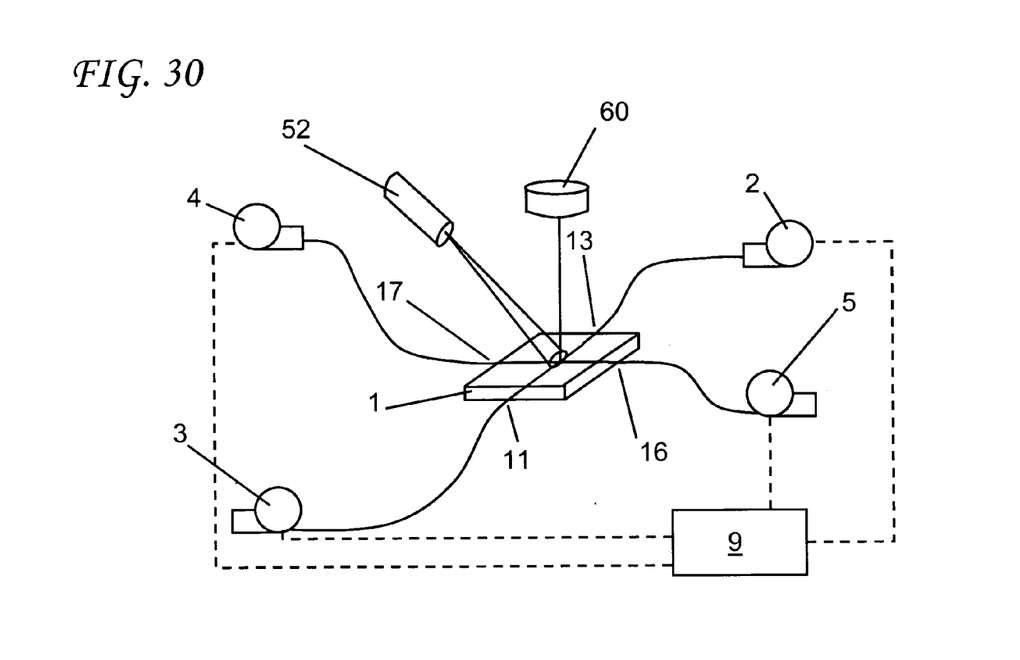
FIGS. 30 and 31 show systems of the invention.

FIG. 30 shows a system of the invention. It comprises processing chamber 1, into which samples are introduced and removed by pumps 2 and 3, and positioning fluid is introduced and removed by pumps 4 and 5. Received particles are illuminated by light source 52 and produce signals which are received by detector 60. The various parts of the system are controlled by controller 9.

Figure 31:
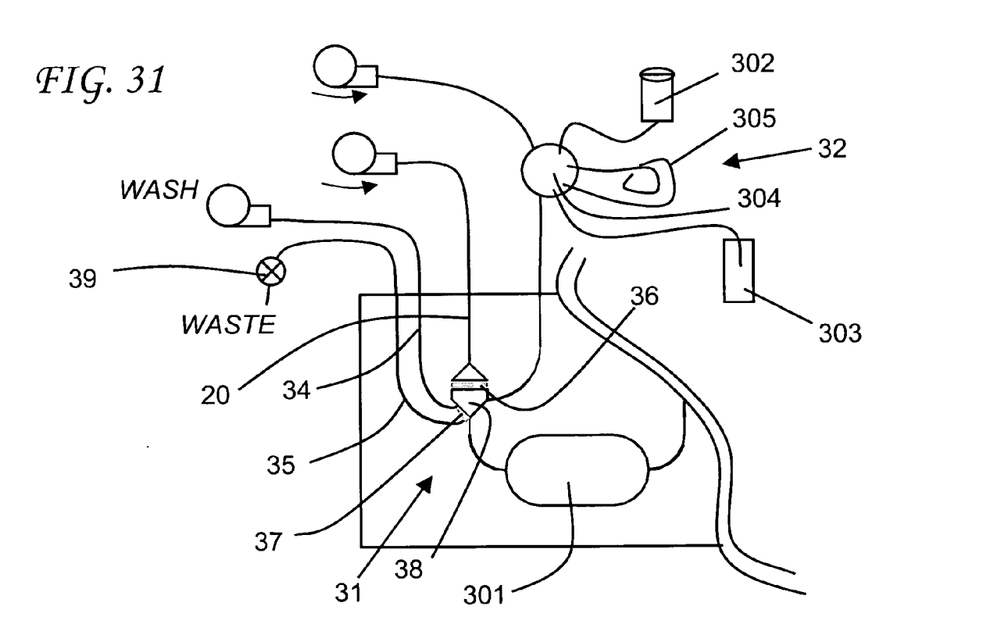

FIG. 31 shows a system of the invention in which the particles are pretreated before being processed. The sample is introduced through a sample loop assembly 32 that is in the line from the sample introduction pump to the processing chamber. The loop assembly comprises sample inlet port 302, a multiport rotor valve 304 with a sample loop 305, and a waste conduit to a waste reservoir 303. With the valve in the first (sample introduction) position the loop is in line with the sample port and waste lines. An excess of sample is introduced through 302 into the sample loop 305 with the overflow going to waste 303. Once the sample is introduced, the valve is switched to a second position (run position) in which the sample loop is in the line between the sample introduction pump and the processing chamber, thereby allowing the pump to push the fluid from the loop 305 towards the processing chamber.

The sample passes through conduit 32 into chamber 36 and the excess fluid is allowed to flow to the waste reservoir over weir 37 (which does not allow particles to pass) through conduit 35. An optional shutoff valve 39 is shown. Once the particles have been collected along the weir 37, wash fluid is introduced through conduit 34 to wash off excess components of the assay mixture. The wash fluid can for example contain reactants that are necessary for an assay, in which case the wash fluid flows across the particles for the length of time necessary to complete the reaction. The wash line can be connected to a manifold (not shown) which is connected to a plurality of reactant mixtures, so that a series of chemical reactions can be carried out. The progress of the reaction(s) can in some cases be monitored by observing signals from the particles (for example if appropriate fluors are added as part of the reaction sequence). The wash line can be placed at other positions in the chamber 37. Again, the fluid from the wash reservoir passes out of the chamber over the first weir through the conduit 35 to the waste reservoir.

Once the particles have been washed, they can be moved from the weir 37 to a second weir 36 by flowing wash fluid through conduit 34 through the chamber over the second weir and through conduit 20 for a short time. Once the particles have been placed on weir 36, they can be moved towards the processing chamber by sending fluid through conduit 20. As the particles move towards the processing chamber, they pass through a dilution chamber 301, in which the particles distribute themselves as the fluid expands into the dilution chamber. The volume of the dilution chamber serves as a liaison between the particle density received into the particle analysis system from the assay and the particle density that is optimum for the number of particle parking sites in the EPRP.

The invention claimed is:

1. A method for processing particles comprising the steps of:
   A) placing a sample containing said particles dispersed in a liquid into a processing chamber comprising:
      i) an inlet;
      ii) an elongate particle retention passage (EPRP) having first and second ends, said EPRP being in liquid communication with said inlet;
      iii) an elongate particle receptor located between said first and second EPRP ends, said elongate particle receptor comprising:
         an elongate barrier member for permitting liquid passage while preventing passage of particles to be processed, said barrier being a weir and the only way in which liquid can pass said barrier member being over said weir; and,
      iv) an elongate retention member adjacent said weir and forming an elongate corner with said weir;
   B) causing at least some of said particles in said placed sample to be received by said particle receptor so that said received particles are all in the same plane; and,
   C) processing at least some of said particles received by said particle receptor.

2. The method of claim 1 wherein step D) comprises removing said particles from said processing chamber so that the processing chamber can be reused.

3. The method of claim 1 wherein substantially all of said particles in said sample are substantially a same size, said size ranging from 0.1 micron to 50 microns.

4. The method of claim 1 wherein the EPRP has a width of about 40 to 100 microns and a depth of 10 to 50 microns.

5. The method of claim 1 wherein said weir and said retention member each include a plurality of pockets, each pocket able to receive only one of said particles.

6. The method of claim 1 wherein step B) further comprises pumping a positioning liquid through said processing chamber to direct said particles toward said particle receptor.

7. The method of claim 1 wherein step B) further comprises flowing said liquid sample to direct said particles towards said particle receptor.

8. The method of claim 1 wherein step C) further comprises simultaneously exposing substantially all of said particles received by said particle receptor to electromagnetic radiation to elicit a response from said received particles that provides information about said received particles.

9. The method of claim 8 wherein substantially all of said received particles are subject to confocal examination.

10. The method of claim 1 wherein step C) further comprises subjecting said received particles to conditions that cause a chemical reaction of the particles.

11. A processing chamber for processing particle-containing liquid samples, said processing chamber comprising:
    A) a sample inlet;
    B) an elongate particle retention passage (EPRP) having first and second ends, said EPRP in fluid communication with said inlet;
    C) an elongate particle receptor located between said first and second ends of said EPRP, said elongate particle receptor comprising:
       i) an elongate barrier member, said barrier member being a weir that permits passage of liquid but not passage of particles having a size greater than a selected sized in the range of 1 to 20 microns; and,
       ii) an elongate retention member adjacent said weir and forming an elongate corner with said weir, said retention member comprising a plurality of pockets, each pocket having a maximum depth of about 2 to about 20 microns and a width of about 3 to 50 microns.

12. The processing chamber of claim 11 wherein the EPRP has a transverse dimension of 10 to 100 microns.

13. The processing chamber of claim 11 wherein said EPRP has a width of about 40 to about 100 microns and a depth of 10 to 50 microns.

14. A method for processing particles, the method comprising the steps of:
    A) providing a processing chamber comprising:
       i) an inlet;
       ii) an elongate particle retention passage (EPRP) having first and second ends, said EPRP being in fluid communication with said inlet;
       iii) an elongate particle receptor located between said first and second EPRP ends comprising an elongate barrier member that permits passage of liquid but not passage of said particles for processing, wherein said barrier member is a weir and the only way that liquid can pass the barrier member is over the weir, i. wherein the particle receptor comprises an elongate retention member adjacent said weir and forms an elongate corner with said weir, and at least one of said weir and said retention member includes a plurality of pockets, each of said pockets being capable of receiving only one of said particles;

B) placing a sample containing said particles dispersed in a liquid into said processing chamber;

C) causing at least some of the particles in said placed sample to be received by said particle receptor so that said received particles are all in the same plane;

D) processing at least some of said particles received by said particle receptor; and, E) discarding said processing chamber containing said particles after step D).

* * * * *